United States Patent [19]
Honkawa et al.

[11] Patent Number: 5,646,738
[45] Date of Patent: Jul. 8, 1997

[54] SYSTEM FOR DETERMINING DAMPENING WATER FOR AN OFFSET PRESS USING CONVENTIONAL CATOPTRIC LIGHT INTENSITY

[75] Inventors: Yoshinori Honkawa; Takashi Sakaguchi, both of Fuchu, Japan

[73] Assignee: Ryobi, Ltd., Japan

[21] Appl. No.: 705,069

[22] Filed: Aug. 29, 1996

Related U.S. Application Data

[63] Continuation of Ser. No. 360,009, Dec. 20, 1994, abandoned.

[30] Foreign Application Priority Data

Dec. 20, 1993 [JP] Japan ................... 5-320044

[51] Int. Cl.$^6$ .................... G01N 21/55; G01N 21/85
[52] U.S. Cl. .................... 356/445; 101/DIG. 45
[58] Field of Search .................... 356/445, 446; 101/DIG. 45

[56] References Cited

U.S. PATENT DOCUMENTS

| | | | |
|---|---|---|---|
| 4,052,937 | 10/1977 | Lawson et al. | 356/445 X |
| 4,565,450 | 1/1986 | Wirz et al. | 356/446 X |
| 4,737,035 | 4/1988 | Aoki et al. | 356/446 X |
| 5,108,186 | 4/1992 | Kipphan et al. | 356/445 X |
| 5,162,865 | 11/1992 | Kipphan et al. | 356/446 X |

Primary Examiner—Vincent P. McGraw
Attorney, Agent, or Firm—Merchant, Gould, Smith, Edell, Welter & Schmidt

[57] ABSTRACT

A LED radiates light on a plate held on plate cylinder upon receiving a radiation start signal, so as to form an irradiated area on plate. A photo diode (PD) senses substantially only conventional catoptric light reflected from irradiated area and generates the sensed signal representing the conventional catoptric light intensity. A data processing unit computes the dampening volume based on the sensed signal which is stored in storage device 9, storage device 9 then generates dampening volume signal. The LED is held in such manner that an incident angle of the light in connection with the surface of the irradiated area is made at predetermined angle sufficient for changing the conventional catoptric light intensity sensed by PD in accordance with the dampening volume.

15 Claims, 18 Drawing Sheets

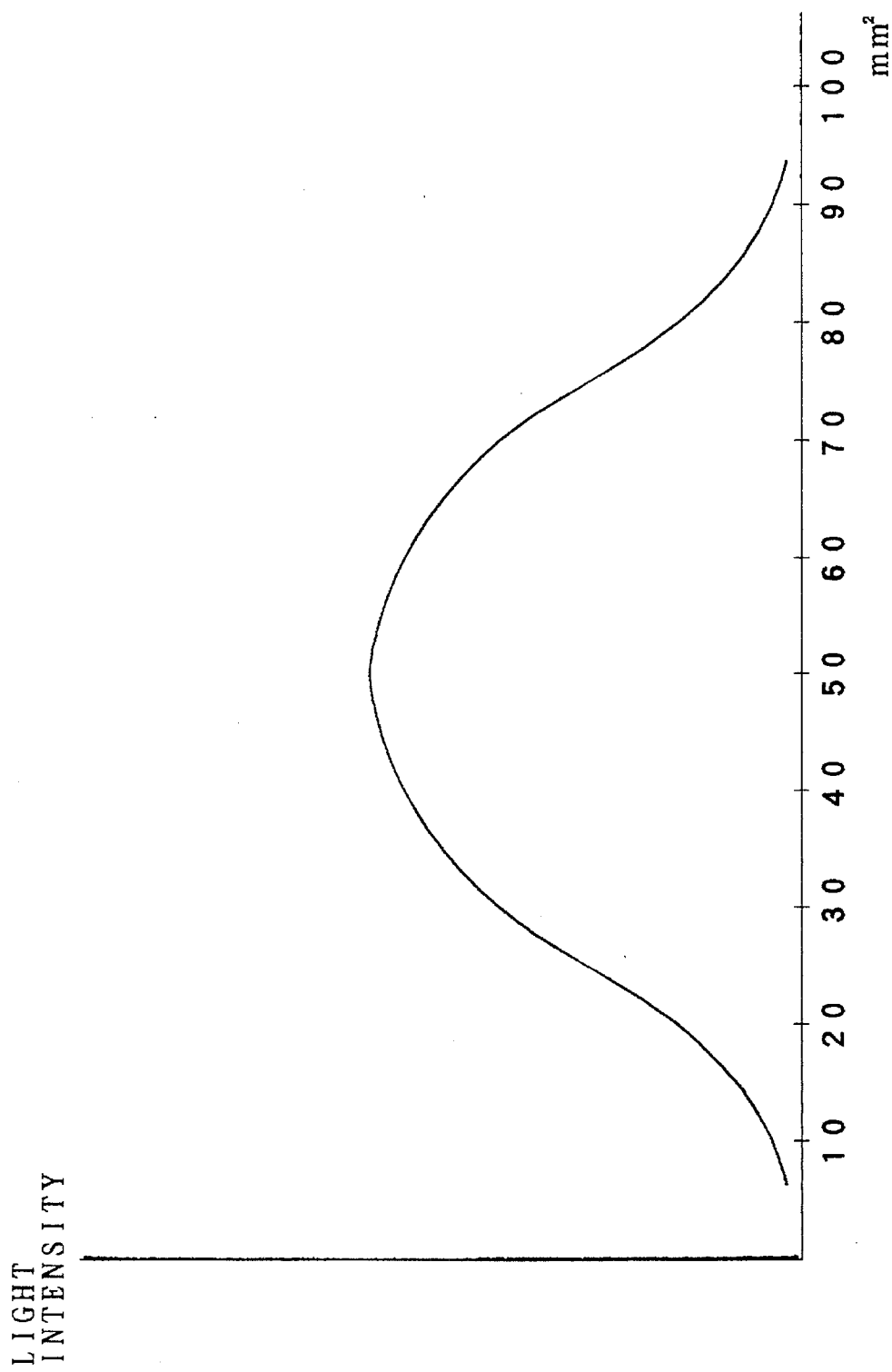

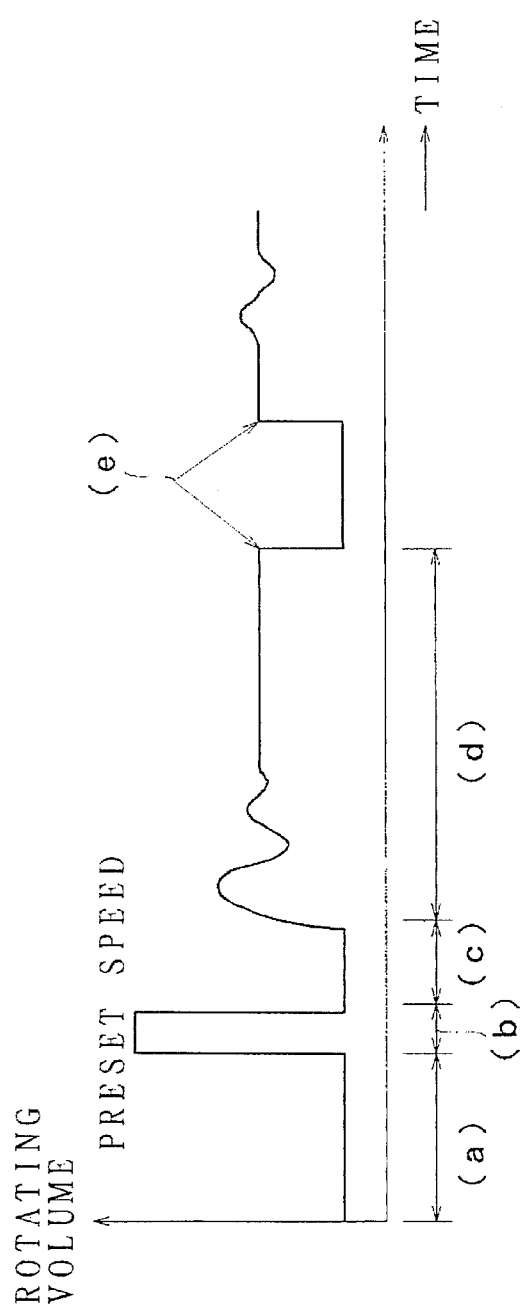
F I G. 17A
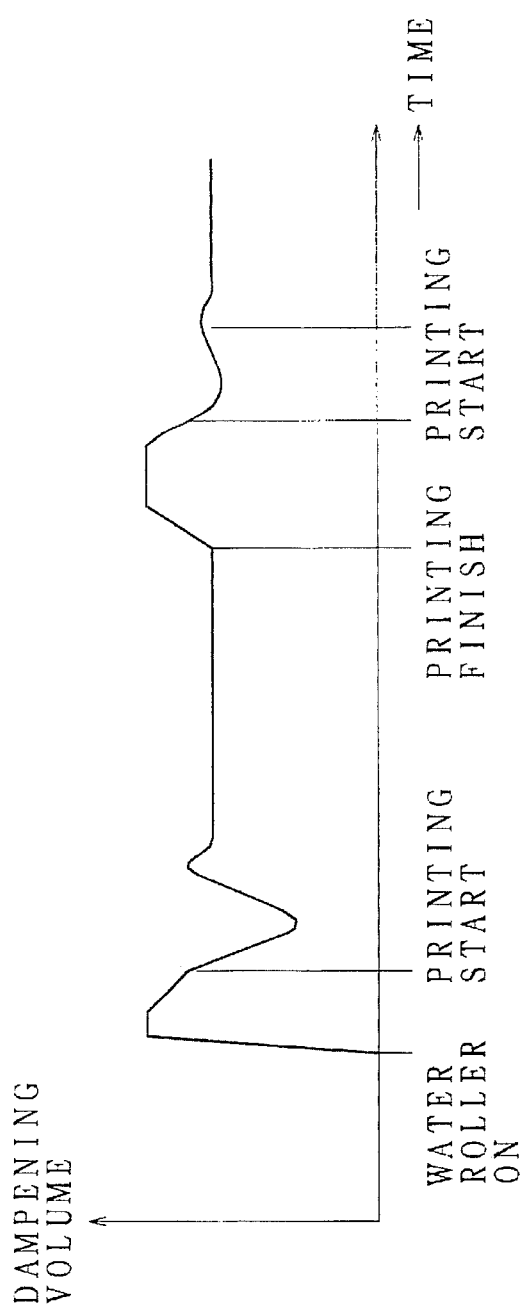
F I G. 17B 5,646,738

SYSTEM FOR DETERMINING DAMPENING WATER FOR AN OFFSET PRESS USING CONVENTIONAL CATOPTRIC LIGHT INTENSITY

This is a Continuation of application Ser. No. 08/360,009, filed Dec. 20, 1994, now abandoned.

TECHNICAL FIELD OF THE INVENTION

This invention relates to a dampening volume control device for offset press, and more particularly to detection of the dampening volume.

BACKGROUND OF THE INVENTION

A dampening volume control device is used in an offset press in order to control dampening volume. The dampening volume control device detects the dampening volume of a plate held on a plate cylinder and keeps the dampening volume in accordance with an operator's order in order to prevent a change in the quality of print caused by changing the dampening volume.

One existing dampening volume control device is shown in FIGS. 1A and 1B. The dampening volume is detected by measuring the intensity of a catoptric light reflected from the plate. Specifically, a light emitting diode (LED) radiates light towards the plate at a predetermined angle forming an irradiated area thereon. The light is reflected on the irradiated area. The catoptric light reflected from the plate is then sensed by a photo diode (PD). Generally, the intensity of the catoptric light decreases with reduction of the dampening volume as is shown in FIG. 1A, and increases with addition of the dampening volume as is shown in FIG. 1B.

The intensity of a conventional catoptric light, however, is not always directly proportional to the dampening volume. Therefore, the dampening volume can not be sensed exactly.

Japanese Patent Laid-open Publication NO. SHO 62-75305 discloses a dampening volume sensing device which helps solve this problem. The dampening volume sensing device 100 includes a first sensor 114 which is symmetrically arranged with a LED 112, a second sensor 115 which senses the unconventional catoptric light, and a third sensor 119. The dampening volume sensing device 100 senses a more accurate dampening volume than the device of FIG. 1A and 1B by adjusting the intensity of the conventional catoptric light sensed by the first sensor 114 using the intensity of unconventional catoptric light sensed by the second sensor 115.

The dampening volume sensing device of FIG. 2, however, has several disadvantages. To begin with, it requires a complex structure and configuration. With such a dampening volume sensing device, all the light reflected by the irradiated area must be sensed by the first sensor 114 and the second sensor 115. In order to do so, the third sensor 119 must be provided to set the irradiated area to an intersecting point of an axis of both the first sensor 114 and the second sensor 115. This is accomplished by adjusting the distance d between the third sensor 119 and the plate 13 until the light intensity sensed by the third sensor 119 is a maximum. Furthermore, as is shown in FIG. 3, the light intensity in a sensing point 140 differs from a light intensity in a sensing point 142 due to a grainy form.

SUMMARY OF THE INVENTION

The present invention solves the above-mentioned problems and provides a dampening volume sensing device having a simple structure, which accurately senses a dampening volume and which prevents differences in light intensity based on the location sensing point. One aspect of the present invention relates to a dampening volume sensing device for an offset press which comprises a light radiating device for radiating light onto a plate held on a plate cylinder so as to form an irradiated area on the plate; a sensor for sensing substantially only conventional catoptric light reflected from the irradiated area and for generating a sensed signal representing the conventional catoptric light intensity sensed; and a for computing the dampening volume based on the sensed signal generated by the sensor and for generating a dampening volume signal. The light radiating device is held such that the light is directed at the surface of the irradiated area at a predetermined angle sufficient for changing the conventional catoptric light intensity sensed by the sensor in accordance with the dampening volume.

A method for sensing the dampening volume of an offset press is also disclosed. The method, involves, radiating light on a plate held on a plate cylinder so as to form an irradiated area thereon; sensing substantially only conventional catoptric light reflected from the irradiated area and generating a sensed signal representing conventional catoptric light intensity; and computing the dampening volume based on the sensed signal and generating a dampening volume signal. The light is radiated at a predetermined angle with respect to the irradiated area which is at a predetermined angle with respect to sufficient for changing the conventional catoptric light intensity in accordance with the dampening volume.

Another aspect of the present invention relates to a dampening volume sensing apparatus for an offset press which comprises the dampening volume sensing device. The apparatus comprises a mechanism for driving the plate cylinder, the dampening volume sensing device being supported so as to be able to move in parallel with an axis of the plate cylinder; an aiming mechanism for searching a proposed area of the plate; a storage device for storing a positional phase defined between the proposed area and a radiating area radiated by the dampening volume sensing device; a detector for detecting a rotating phase of the plate cylinder; and a mechanism for transmitting the radiation start signal to the dampening volume sensing device based on the detected rotating phase of the plate cylinder and the positional phase so that light is radiated on the proposed area in synchronization with the rotation of the plate cylinder.

Yet another aspect of the present invention relates to a dampening volume sensing apparatus which comprises a mechanism for driving the plate cylinder; a mechanism for moving the dampening volume sensing device in parallel with an axis of the plate cylinder; a storage device for storing a reference light intensity which is detected in a non-image area under the no dampening condition in the plate; a searching mechanism for transmitting the radiation start signal to the dampening volume sensing device and for searching a proposed area which has a light intensity substantially the same as the reference light intensity and being wider than the irradiated area, by comparing the reference light intensity with the light intensity detected by the dampening volume sensing device; and a mechanism for generating the radiation start signal to the dampening volume sensing mechanism so that light is radiated on the plate in synchronization with the rotation of the plate cylinder.

Yet a further aspect of the present invention relates to a dampening volume controlling apparatus for an offset press which comprises the dampening volume sensing device and a mechanism for inputting a desired dampening volume on printing; a mechanism for generating an operation signal based on the dampening volume sensed by the dampening volume sensing device and the desired dampening volume on printing; and a control for controlling supply dampening volume to the plate in accordance with the operation signal, so that the sensed dampening volume is approximately the same as the desired dampening volume on printing.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 6 is a graph illustrating the relationship between light intensity and the size of an irradiated area;

FIGS. 17A and 17B are graphs illustrating a change of dampening volume when adjusted by a dampening volume control apparatus of the present invention.

DETAILED DESCRIPTION OF THE PREFERRED EMBODIMENTS

Figure 1A:
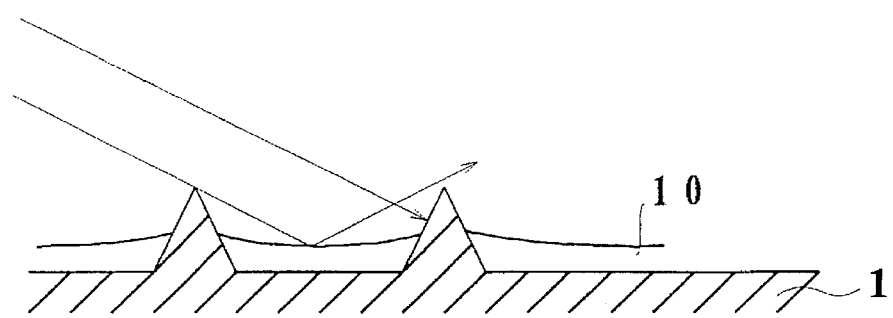
FIGS. 1A and 1B are perspective views of a prior art dampening volume sensing device.
Figure 1B:
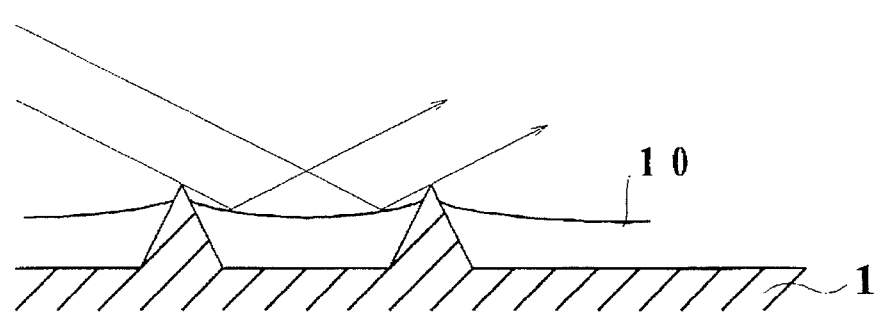
Figure 2:
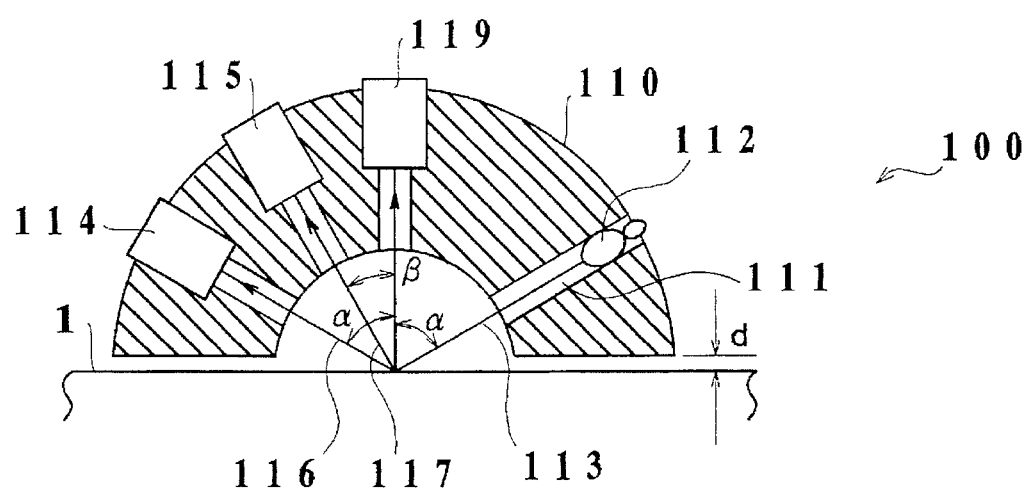
FIG. 2 is a perspective view of another prior art dampening volume sensing device.
Figure 3:
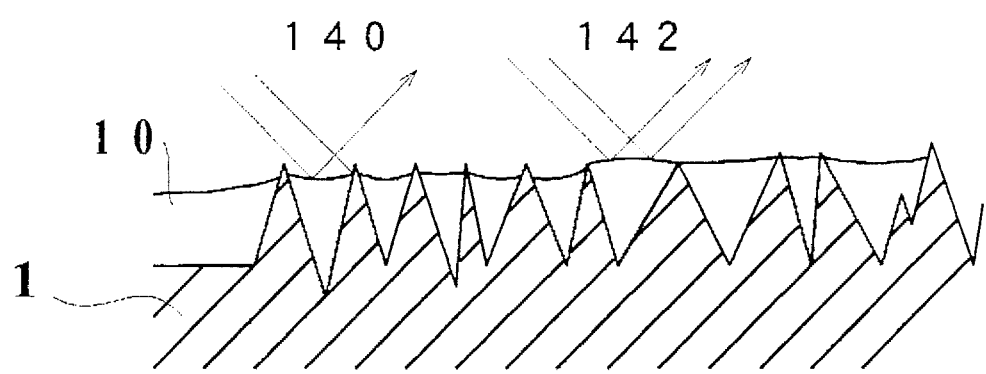
FIG. 3 is a perspective view of a dampening volume sensing device having a grainy form.
Figure 4:
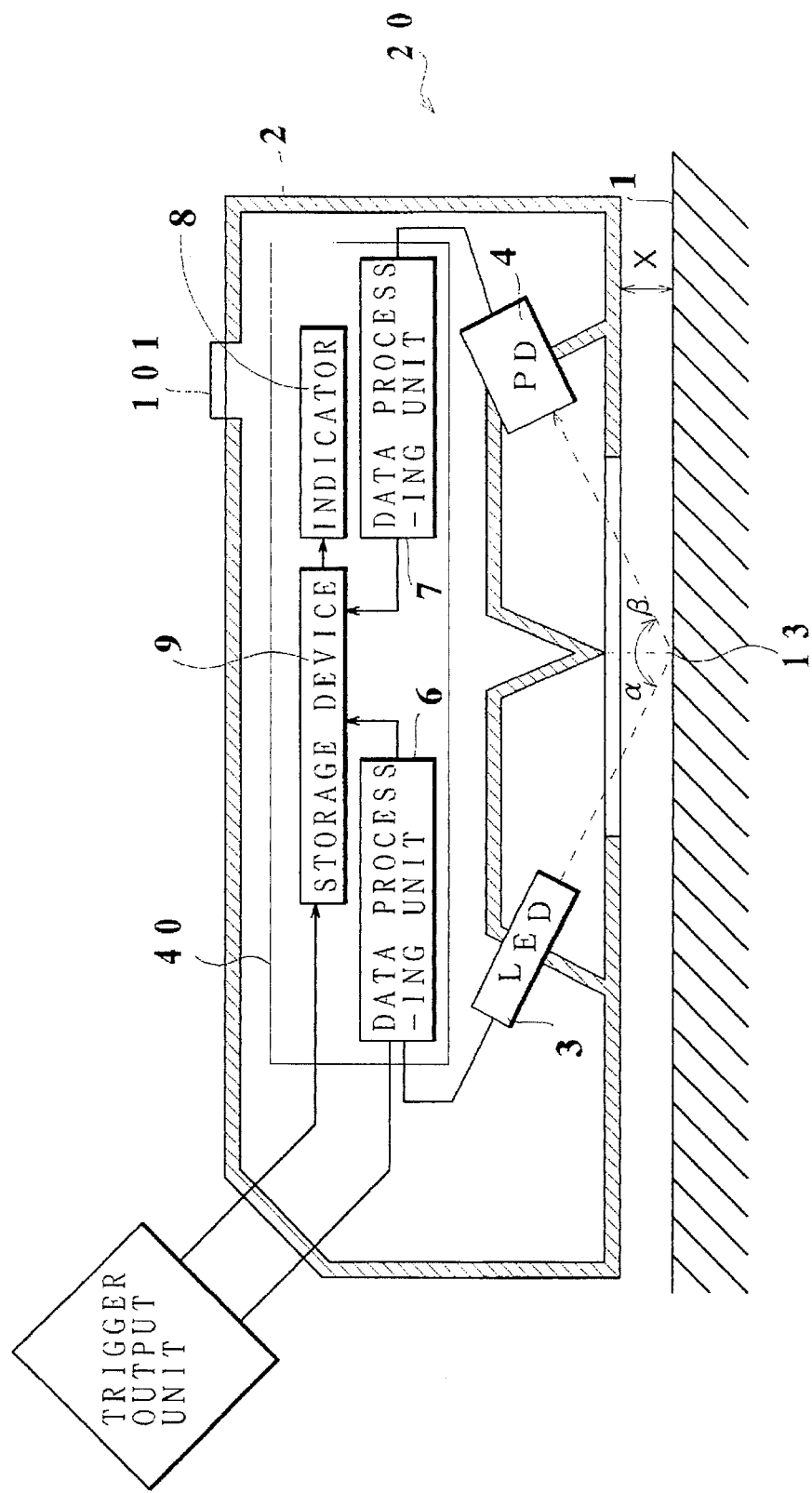
FIG. 4 is a view of one embodiment of a dampening volume sensing device 20 in accordance with the present invention.

Embodiment of a dampening volume sensing device in accordance with the present invention will now be described with reference to Figures. In particular, FIG. 4 shows a dampening volume sensing device 20 which comprises an LED 3 which acts as a light radiating device, a photo diode (PD) 4 which acts as a sensor, a data processing unit 6 for the LED 3, a data processing unit 7 for the PD 4 which performs calculations, an indicator 8 and storage device 9. Data processing units 6 and 7, indicator 8 and storage device 9 are fabricated on a substrate 40, which is contained in a housing 2.

Figure 5A:
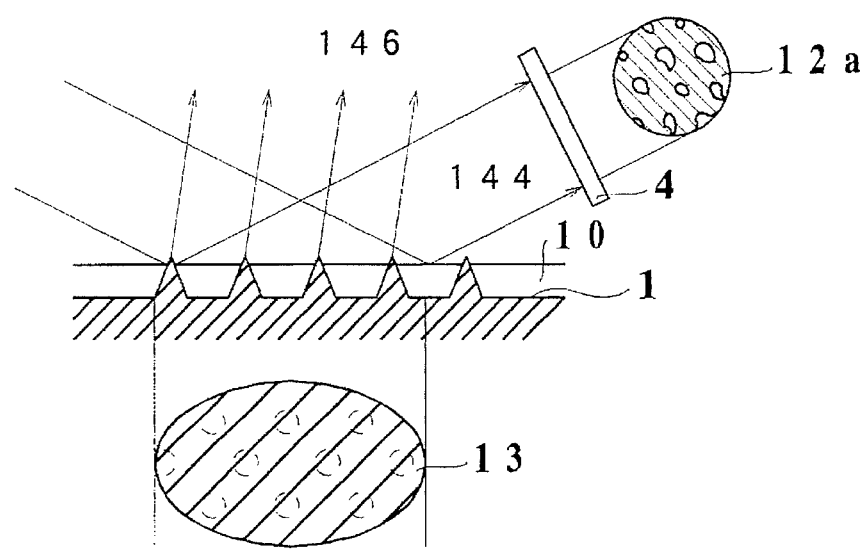
FIGS. 5A and 5B are perspective views for disclosing a relationship between light intensity and dampening volume.

LED 3 directs light towards a presensitized offset plate (PS-plate) 1 of an offset press, thereby forming an irradiated area 13 on PS-plate 1. The angle of incidence of the light to irradiated area 13 is referred to as angle $\alpha$. When the angle of incidence of the light is substantially equal to its angle of reflection, the light is referred to as conventional catoptric light. An example of such light is shown in FIG. 5A as 144.

LED 3 is positioned within housing 2 so that most of the light radiating therefrom is unconventional catoptric light (i.e., its angle of incidence is not substantially equal to its angle of reflection). An example of unconventional catoptric light is shown in FIG. 5A as 146.

Preferably, angle $\alpha$ ranges between 65° and 85°. More preferably, angle $\alpha$ ranges from 70° to 80°. Most preferably angle $\alpha$ is about 75° in order to develop a large amount of unconventional catoptric light the irradiated area 13.

While the light radiating device is shown as an LED, it is understood by those skilled in the art that other light radiating devices may be used, such as, for example, a LASER diode or an electric bulb. The radiating mechanism may also be used in conjunction with an optical fiber cable, or mirrors.

PD 4 generates a sensed signal representing the conventional catoptric light intensity. PD 4 is oriented within housing 2 so that an axis of LED 3 and an axis of PD 4 are symmetrical with respect to a line perpendicular to irradiated area 13. For example, if the angle of incidence of the light radiated by LED 3 is 75°, the axis of PD 4 is 75° from the line perpendicular to irradiated area 13. With such a configuration, PD 4 senses substantially only a conventional catoptric light.

While the sensor is shown as a photo diode, it is understood by one skilled in the art that other sensors can be used, such as, for example, a photo-transistor or charge coupled device (CCD). Like the light radiating device, the sensor also be used in conjunction with an optical fiber cable or mirrors.

A relationship exists between the size of irradiated area 13 and the signal sensed by PD 4 and will be described with reference to FIG. 6. Preferably, the irradiated area formed on the PS-plate 1 is sufficiently large so that substantially only conventional catoptric light is sensed by PD 4 irrespective of whether PS-plate 1 has a grainy form. The size of the irradiated area may be set by adjusting the distance x between dampening volume sensing device 20 and PS-plate 1. In a preferred form, the distance x is set so that the irradiated area ranges between 30 mm² to 70 mm² In a more preferred form, the distance x is set so that the irradiated area is about 50 mm², where the intensity of the signal sensed by PD 4 is at its maximum. A condensing device such as a condensing lens may be provided between the irradiated area and PD 4 when the irradiated area is larger than the sensing size of PD 4.

The sensing operation of device 20 will now be described. The dampening volume is accurately sensed by directing the radiating light at a predetermined angle to a surface of irradiated area 13 sufficient for changing the conventional catoptric light intensity sensed by PD 4 in accordance with the sensed dampening volume.

Data processing unit 6 transmits a radiation start signal to LED 3 upon receiving a trigger signal from trigger output unit 14. LED 3 radiates light onto PS-plate 1 upon receiving the radiation start signal from data processing unit 6. The light radiated from the LED 3 comprises both conventional catoptric light and unconventional catoptric light due to the irregular surface of PS-plate 1, such as the grainy form shown in FIG. 5A. However, by positioning PD 4 within housing 2 so that an axis of LED 3 and an axis of PD 4 are symmetrical with respect to a line perpendicular to irradiated area 13, PD 4 senses substantially only the conventional catoptric light (see FIG. 5A).

The dampening volume of PS-plate 1 is calculated based on the conventional catoptric light radiated by LED 3. Referring back to FIG. 4, data processing unit 7 calculates the dampening volume based on the signal sensed by PD 4. The calculated dampening volume is then stored in storage device 9. Storage device 9 generates a signal corresponding to the calculated dampening volume upon receiving an indicating signal from trigger output unit 14. Trigger output unit 14 generates an indicating signal with every rotation of a plate cylinder 5 (see FIG. 9A). Indicator 8 indicates the calculated dampening volume upon receiving the signal generated by storage device 9.

Figure 5B:
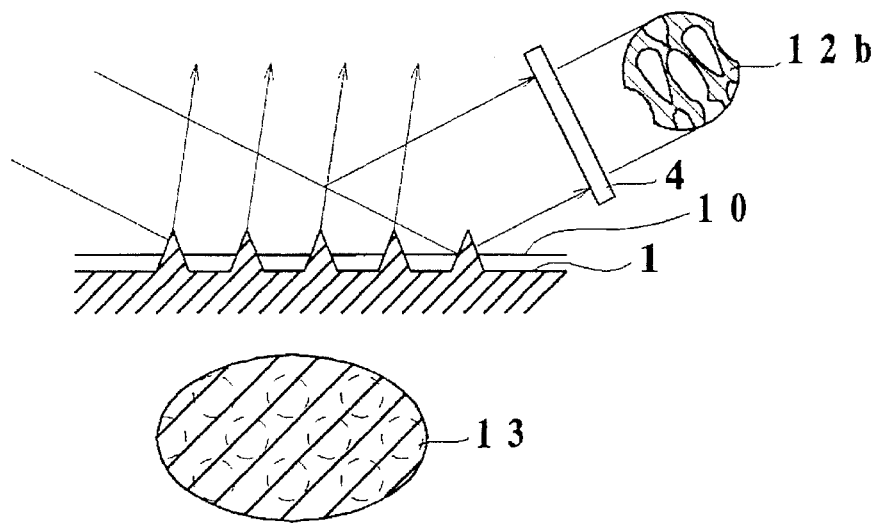

The signal sensed by PD 4 of device 20 varies in proportion to the dampening volume. As shown in FIG. 5A and 5B irradiated area 13 of PS-plate 1 has a grainy form, such as an irregular surface having a height ranging between 5 to 10 μm. The dampening is held in the grainy form. FIG. 5A shows an image 12a sensed by PD 4 when irradiated area 13 holds a large amount of dampening. In particular, hatching area represents the lighted area in which the conventional catoptric light is sensed, while non-hatching area represents the dark area in which the conventional catoptric light is not sensed. When irradiated area 13 holds a large amount of dampening, the intensity of the sensed light is high, since the lighted area is large. FIG. 5b shows an image 12b when irradiated area 13 holds a small amount of dampening. In such areas, the intensity of the sensed light is low, since the lighted area is small.

Figure 7A:
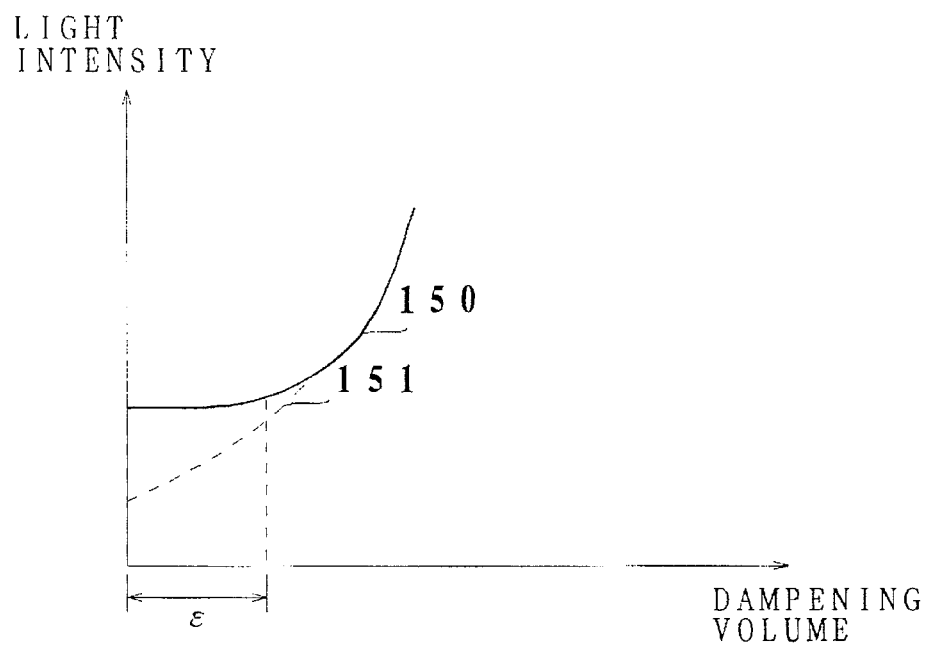
FIGS. 7A and 7B are graphs illustrating the relationship between conventional catoptric light and unconventional catoptric light.
Figure 7B:
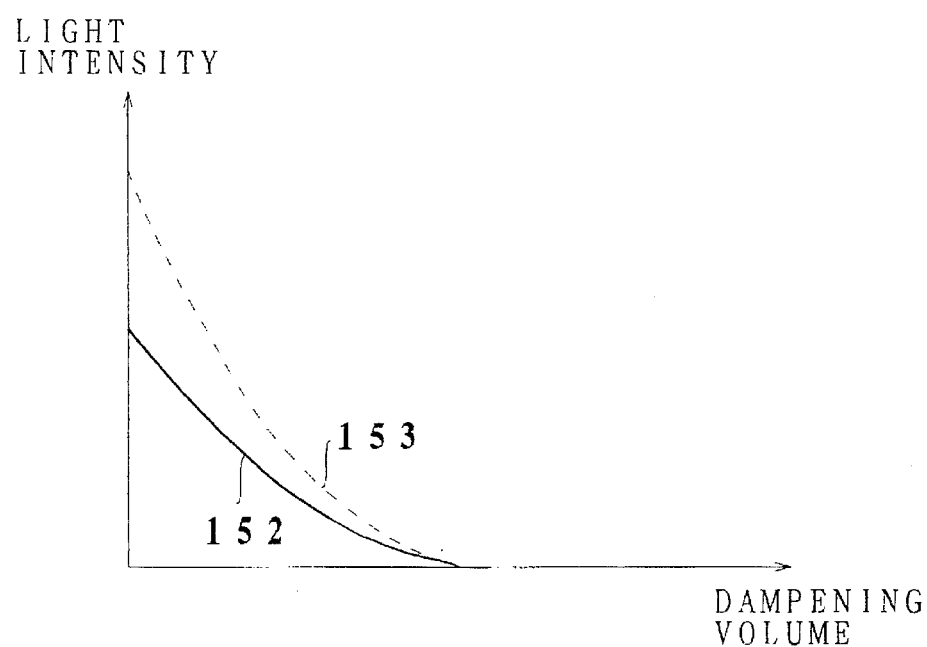

FIGS. 7A and 7B show the relationship between the conventional catoptric and unconventional catoptric light intensity, respectively, for a prior art dampening device and that of the present invention. Curves 151 and 153 represent the conventional catoptric and unconventional catoptric light intensities, respectively, sensed with the dampening volume sensing device of the present invention. Curves 150 and 152 represent the conventional catoptric and unconventional catoptric light intensities, respectively, sensed with the dampening volume sensing device of the prior art. As is shown in FIG. 7A, the conventional catoptric light intensity sensed with the dampening volume sensing device of the present invention varies in accordance with the dampening volume when the dampening volume is small (i.e., range ε). The conventional catoptric light intensity sensed by the dampening volume sensing device of the prior art, however, remains constant when the dampening volume is within range ε. By using a large angle α (see FIG. 4), the conventional catoptric light intensity 151 sensed by PD4 is inversely proportional to the dampening volume so that the conventional catoptric light intensity 151 decreases within range ε.

Figure 8:
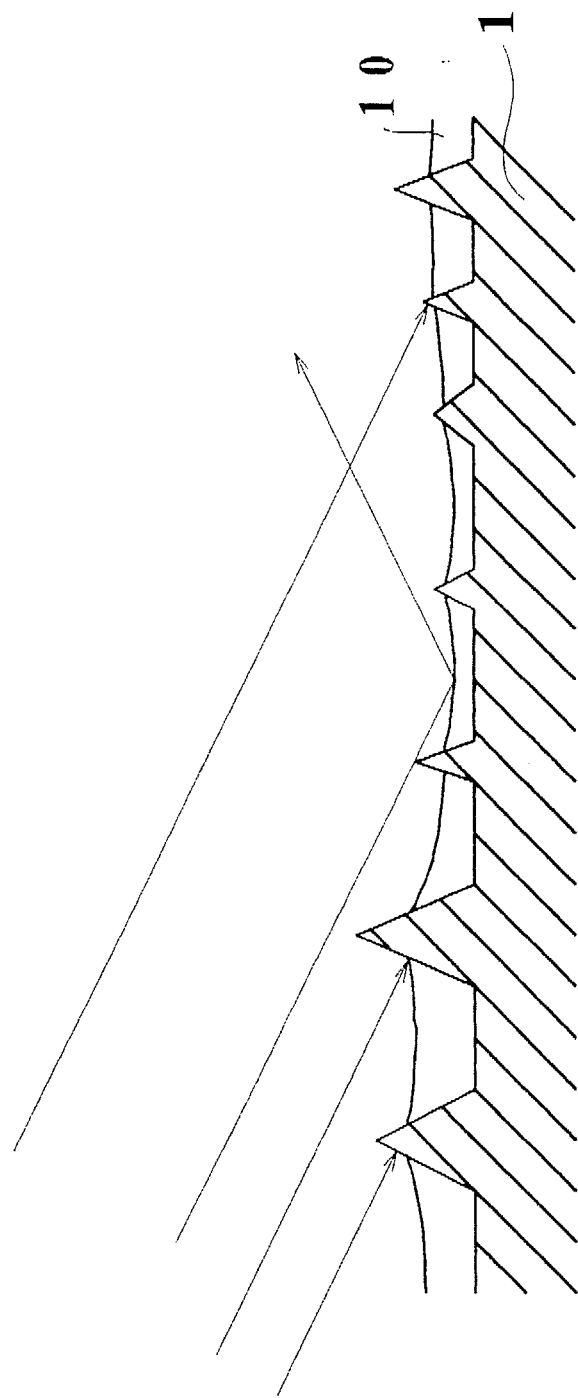
FIG. 8 is a perspective view of a plate having a grainy form.

By keeping irradiated area 13 sufficiently large the dampening volume may be more accurately sensed. FIG. 8 shows a place having a grainy form that varies widely. The light radiated from LED 3 and reflected on the irradiated area is almost entirely unconventional catoptric light when the angle is 75° and the irradiated area is small. Also the intensity of it varies widely depending on the irradiated point, even when the conventional catoptric light is obtained. The conventional catoptric light develops and the dampening volume is accurately and the intensity of it varies marginally even at different irradiated points since irradiated area 13 is of a sufficient size where the conventional catoptric light can be sensed by PD 4 irrespective of the grainy form of the plate. With such a simple structure using a single PD, the conventional catoptric light intensity may be sensed in accordance with dampening volume.

The dampening volume sensing device 20 is further able to prevent differences based on the sensing point. The light radiating device radiates light on the plate held on the plate cylinder upon receiving a radiation start signal, so as to provide an irradiated area on the plate. The sensor senses substantially only conventional catoptric light reflected from the irradiated area and generates a sensed signal representing the conventional catoptric light intensity sensed by the sensor. A data processing unit calculates the dampening volume based on the sensed signal and generates a dampening volume signal. The light radiating device is held in such manner that an incident angle of the light with respect to the surface of the irradiated area is made at a predetermined angle sufficient for changing the conventional catoptric light intensity sensed by the sensor in accordance with the dampening volume. The dampening volume is accurately sensed and also the intensity of it varies marginally even when the irradiated area is different since the irradiated area has a sufficiently large size whereby the conventional catoptric light can be sensed by the sensor irrespective of the grainy form of the plate.

Figure 9A:
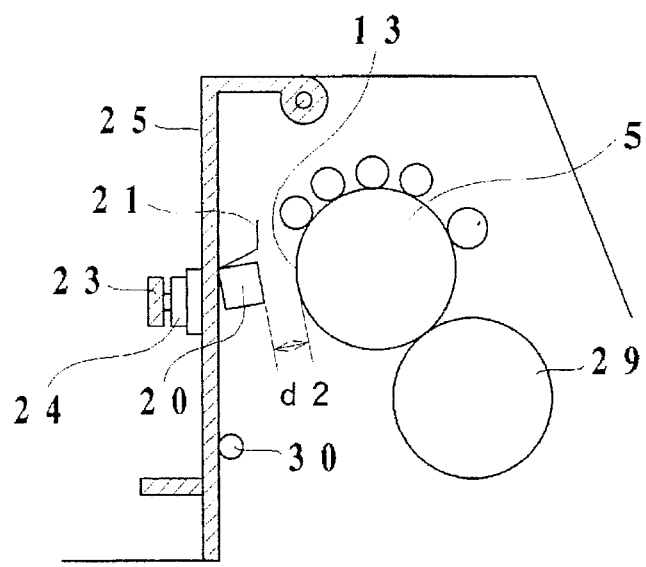
FIGS. 9A and 9B are perspective views of an offset press having a dampening volume sensing device in accordance with the present invention.
Figure 9B:
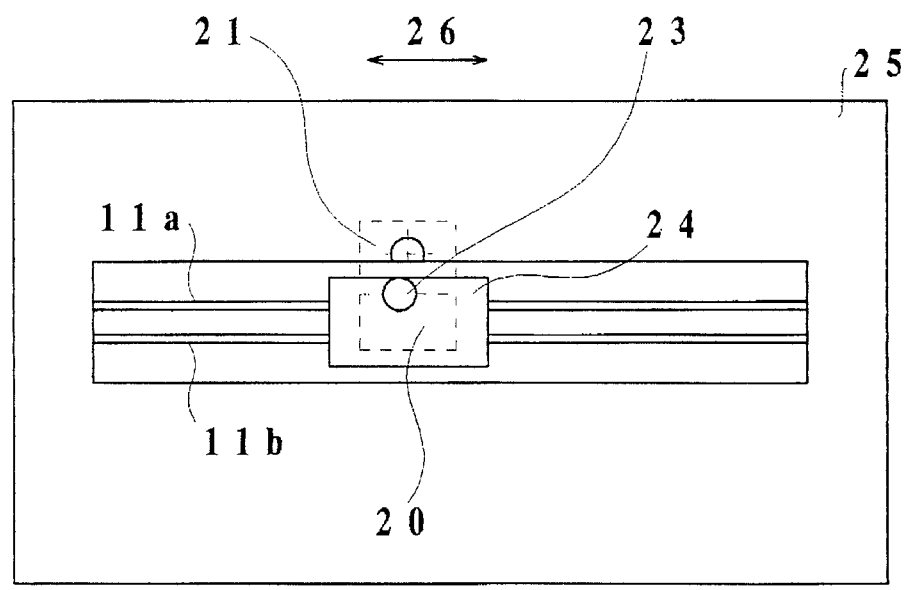

The method of fitting the dampening volume sensing device 20 to the offset press will now be described with reference to FIGS. 9A and 9B. It is possible to sense dampening volume at any point of the plate 13 by moving a slider 24 and rotating plate cylinder 5 as is shown in FIG. 9B. The dampening volume sensing device 20 is fixed within slider 24. Dampening volume sensing device 20 can travel in the direction of arrow 26 along two support rods 11a and 11b. Support rods 11a and 11b are fixed within an opening cover 25 as is shown in FIG.9A Opening cover 25 is held in a predetermined position by a pin 30 in order to establish a distance d2 between dampening volume sensing device 20 and plate 13. In such a manner maintenance of plate 13 may be easily carried out by opening cover 25.

Figure 10:
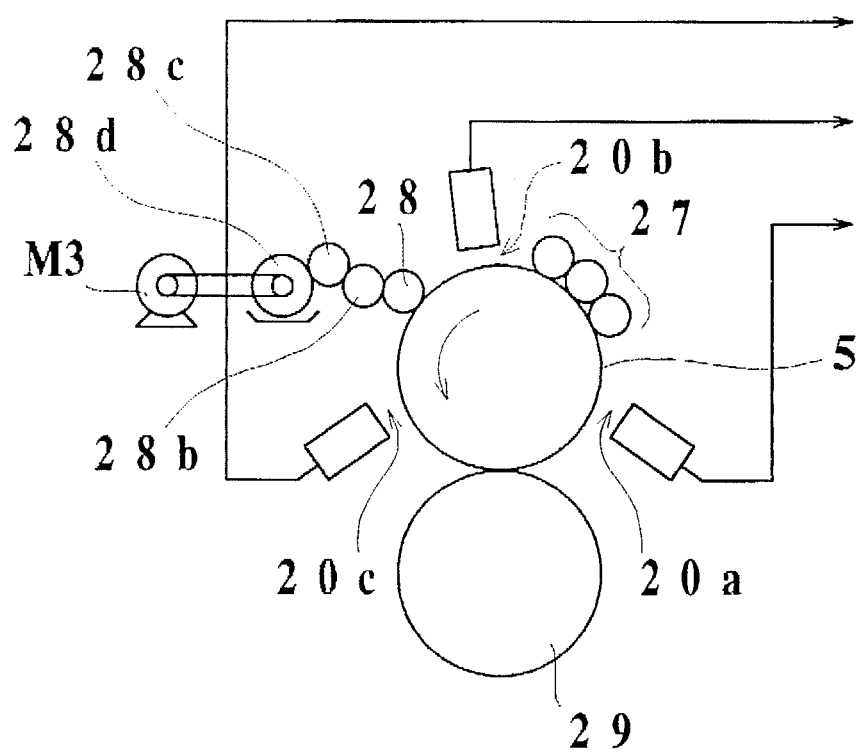
FIG. 10 is a perspective view of an offset press having a dampening volume sensing device in accordance with the present invention.

The positioning of dampening volume sensing device 20 within the offset press will now be described with reference to FIG. 10. Dampening volume sensing device 20 can be fit within the offset press at a variety of positions, such as positions 20a, 20b, 20c or anywhere so long as it does not interfere with the ink roller group 27, the water roller 28 and the blanket cylinder 29. Fitting three dampening volume sensing devices 20 in all the positions 20a, 20b and 20c enables it to more exactly sense the dampening volume of plate 13 caused by providing a volume of ink or by printing action. By fitting dampening volume sensing device 20 in the above-mentioned position, the dampening volume of plate 13 may be detected. The detected dampening volume is given to a control device (not shown).

Figure 11:
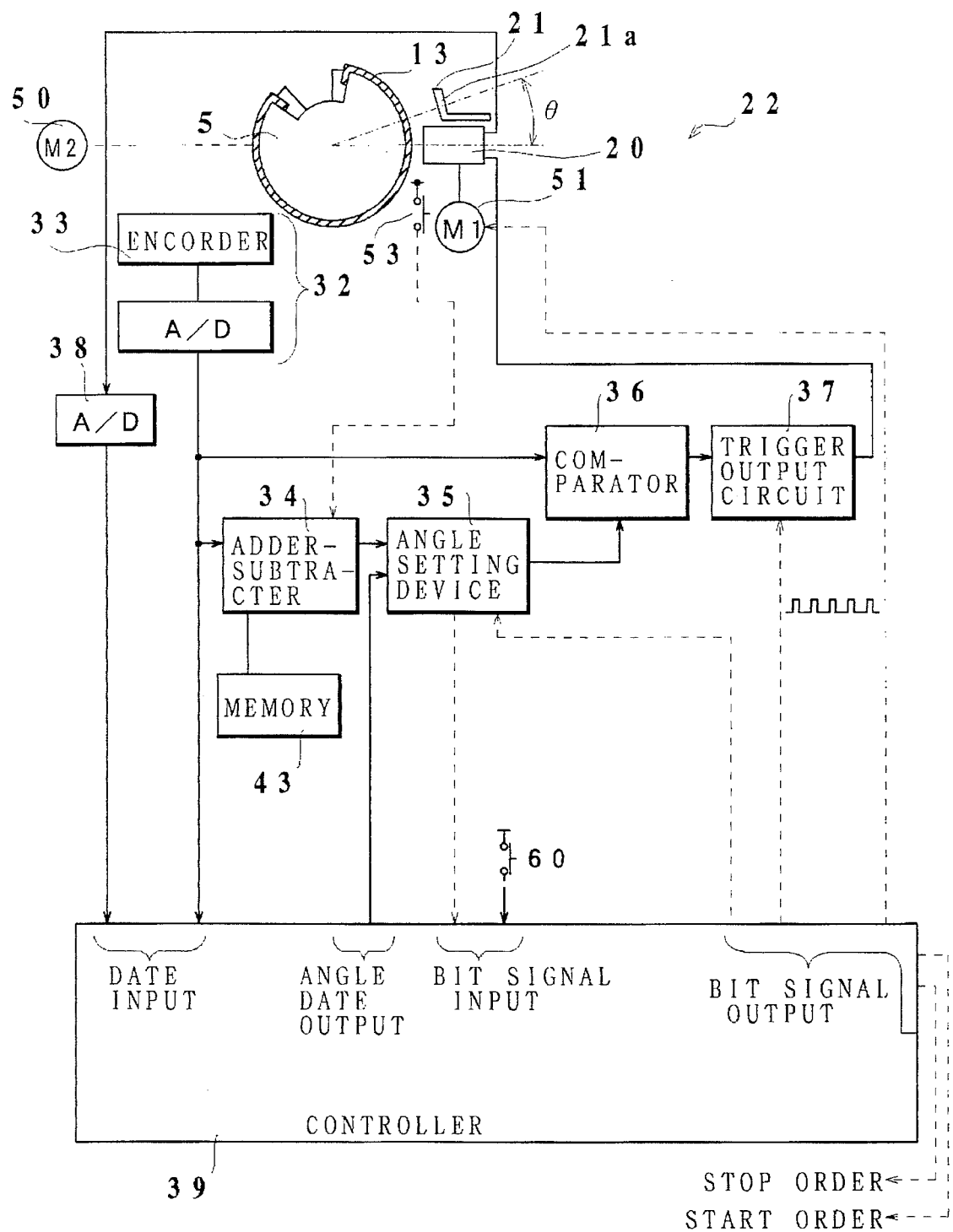
FIG. 11 is a block diagram of a dampening sensing apparatus in accordance with the present invention.

A dampening volume sensing apparatus 22 including the dampening volume sensing device 20 will now be described with reference to FIG. 11. The dampening volume sensing apparatus 22 has a manual setting mode and an automatic setting mode in order to search non-image areas for sensing the dampening volume. The manual setting mode refers to a mode in which an operator searches the non-image area on plate 13. The automatic setting mode refers to a mode for searching the proposed area automatically without the need for an operator. The dampening volume sensing apparatus 22 comprises dampening volume sensing device 20, an indicator 21 for manual operation which acts as an aiming mechanism, a memory 43 which acts as a storage device, a controller 39, an adder-subtracter 34, an angle setting device 35, a comparator 36, and a trigger output circuit 37. Memory 43 stores a positional phase 8 defined between a proposed irradiated area and a radiating area radiated by the dampening volume sensing device. In this embodiment, controller 39, adder-subtracter device 34, angle setting device 35, comparator 36 and trigger output circuit 37 correspond to a generating mechanism for generating a dampening volume signal.

The manual setting mode will now be described with reference to FIGS. 11 and 12. The operator searches the non-image area of plate 13 held on plate cylinder 5. This area is referred to as the proposed area. The operator then looks through a peeping-hole 21a of indicator 21 and searches for the non-image area by rotating plate cylinder 5. The operator stops rotating plate cylinder 5 when the non-image area (proposed area) is found.

Figure 12:
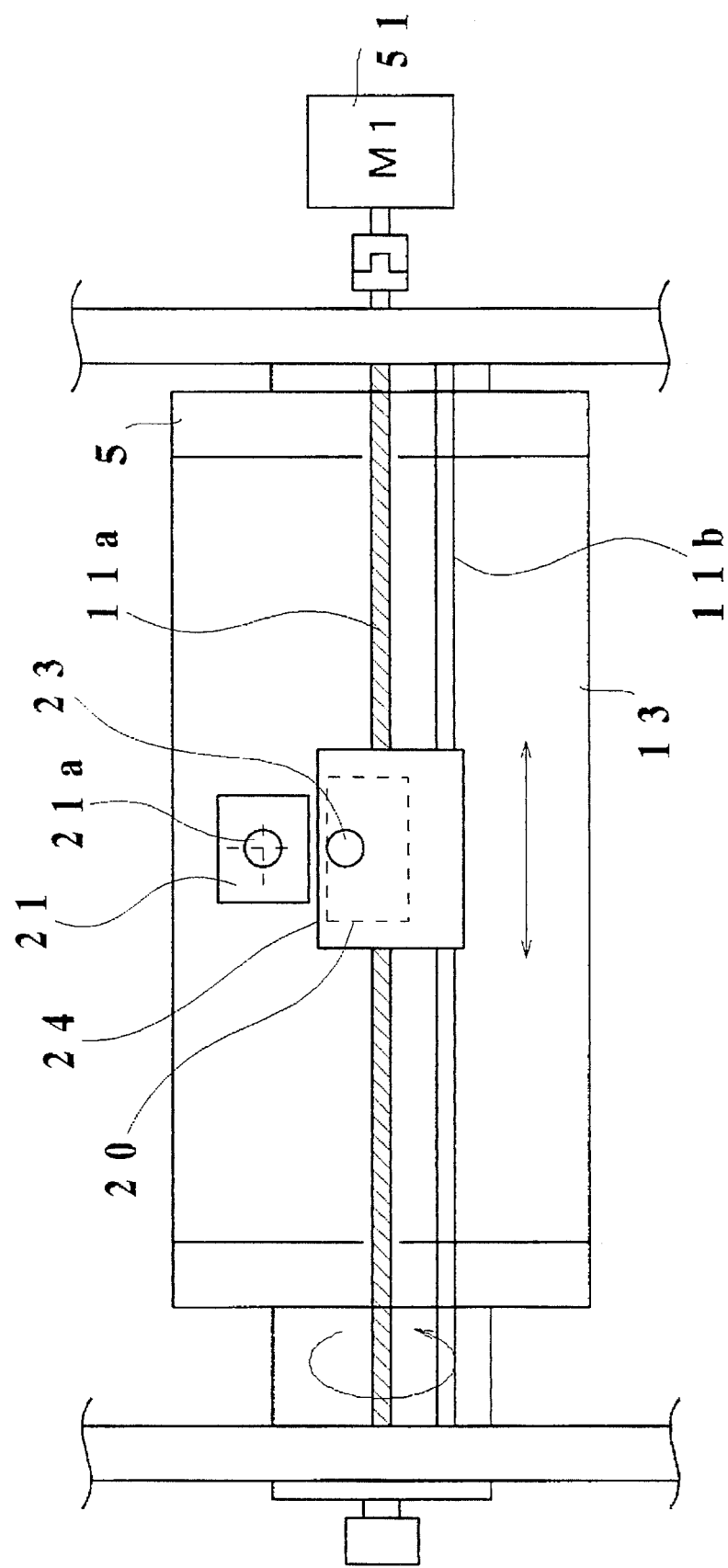
FIG. 12 is a cross sectional of a portion of the offset press of FIG. 11.

If the non-image area is not found on the first rotation, the operator moves indicator 21 in parallel with an axis of plate cylinder 5 as is shown in FIG.12 in order to find the non-image area. The operator may fix slider 24 in place by fastening a stopper bolt 23 when the non-image area is found. The operator thereafter sets a manual setting switch 53 (see FIG. 11) such that a manual setting signal is generated and transmitted to adder-subtracter 34.

Referring back to FIG. 11, an arranged angle value based on the phase 8 at which plate cylinder 5 is rotated is then transmitted to angle setting device 35 upon receiving the manual setting signal. An angle searching device 32 comprises an encoder 33 and A/D converter 38. Encoder 33 is positioned with respect to the axis of the plate cylinder 5 concentrically or in phase with plate cylinder through gears or a belt. The angle searching device 32 determines angle data for plate cylinder 5 and transmits it to controller 39. Controller 39 calculates the amended angle value by using the angle data and the rotating phase and transmits the amended angle value to angle setting device 35.

Light intensity reflected on the proposed area is sensed during every rotation. Plate cylinder 5 is rotated by a motor 50 which acts as a driving mechanism upon receiving a driving signal therefrom. Comparator 36 compares the amended angle value with the angle data and generates a trigger signal to trigger output circuit 37 when the angle data corresponds to the amended angle value. Trigger output circuit 37 gives the radiation start signal for searching to dampening volume sensing device 20. Dampening volume sensing device 20 searches dampening volume upon receiving the trigger signal.

It can be understood by one skilled in the art that the rotating phase is not limited to a fixed value. Indicator 21 and dampening volume sensing device 20 may be arranged so that their positional relationship is adjustable (i.e., phase is adjustable). With such an adjustable structure, indicator 21 can be set in a position so that the operator may peep into plate 13 easily.

The automatic setting mode will now be described with further reference to FIG. 13A for a plate 80 held by plate cylinder 5. As is shown in FIG. 13A, regions 81, 82, 83 and 84 are image areas on plate 80. Motor 51 functions as a moving mechanism and motor 51 functions as a driving mechanism for driving plate cylinder 5 in an automatic setting mode. In this embodiment, controller 39, adder-subtracter 34, angle setting device 35, comparator 36 and trigger output circuit 37 correspond to a generating mechanism.

Figure 13A:
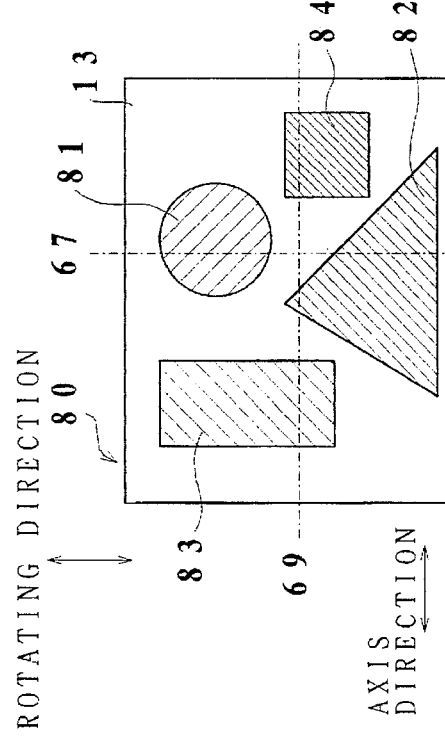
FIG. 13A is a front view of a plate having a plurality of image areas thereon.
Figure 14:
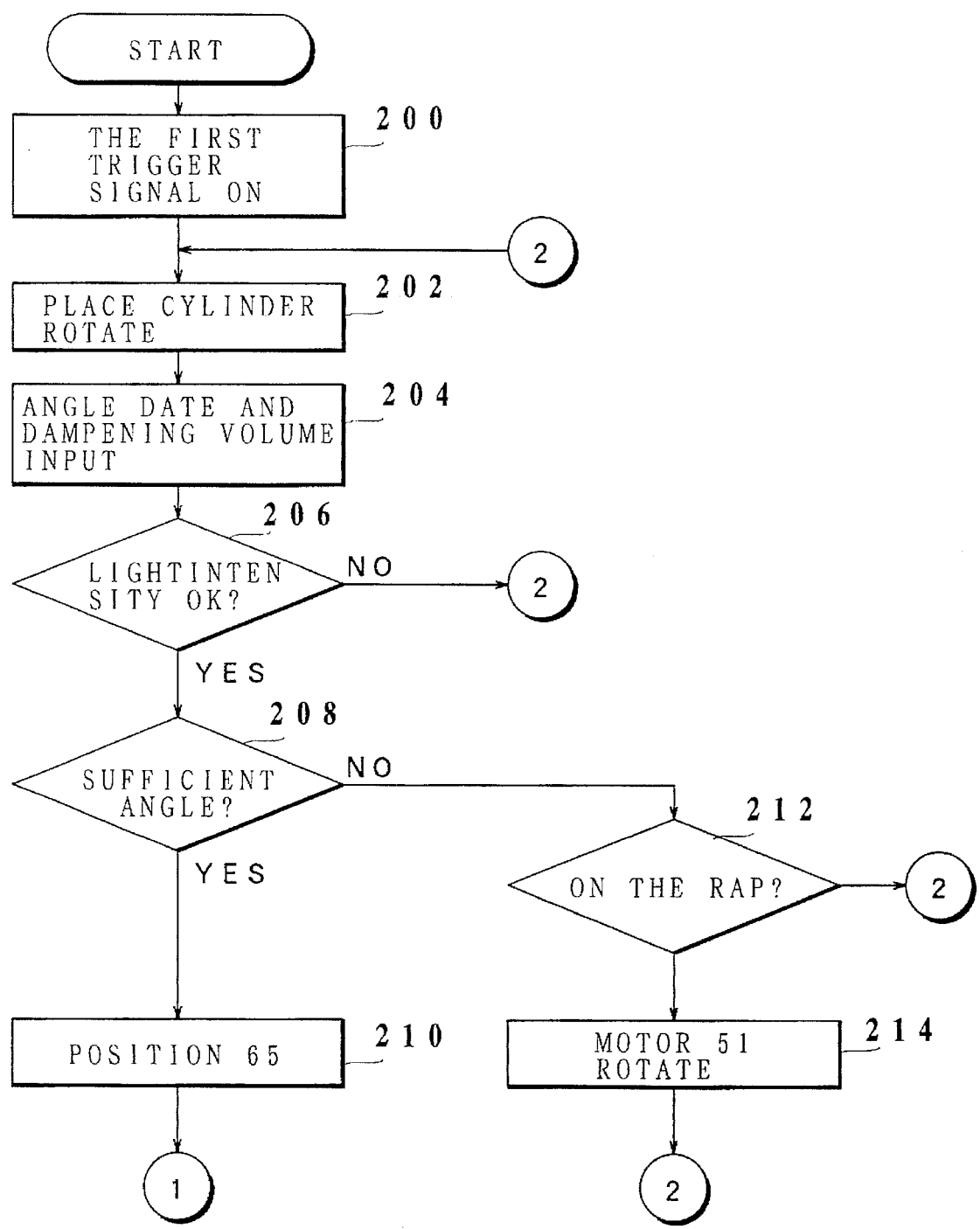
FIG. 14 is a flow chart of an automatic mode for the dampening sensing of FIG. 11.

First, the conventional catoptric light intensity is sensed upon rotating plate cylinder 5. Referring back to FIG. 11, the conventional catoptric light intensity along line 67 of plate 13 (see FIG. 13A) under the no dampening condition is transmitted to controller 39 when a switch 60 for starting the automatic setting mode is set. Referring now to FIG. 14 controller 39 issues the first trigger signal to trigger output circuit 37 at step 200. Plate cylinder 5 is rotated by motor M2 at a predetermined low speed at step 202. Trigger output circuit 37 issues the second trigger signal continuously to dampening volume sensing device 20 upon receiving the first trigger signal. At step 204, dampening volume sensing device 20 senses the conventional catoptric light intensity on the basis of the second trigger signal. The sensed light intensity is converted into digital data by A/D converter 38. The digital data is then transmitted to controller 39. Controller 39 also receives the angle data sensed by angle searching device 32.

Figure 13B:
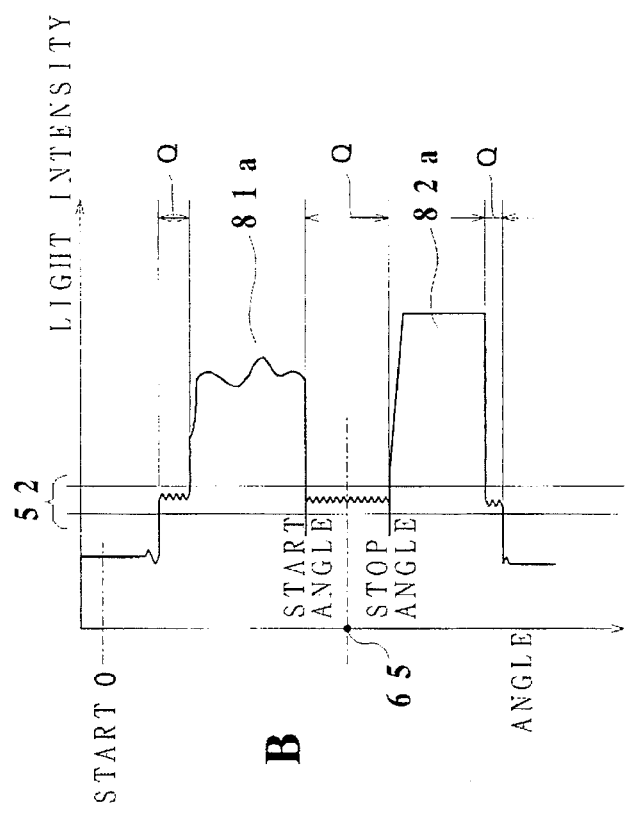
FIGS. 13b and 13c are graphs illustrating the relationship between the light intensity and the angle data and position, respectively, for the plate of FIG. 13A.

A characteristic curve between the light intensity and the angle data is shown in FIG. 13B. The light intensity is greatest at regions 81 and 82 of plate 13 as is represented by 81a and 82b of the curve. The conventional catoptric light is barely sensed at non-image areas under no dampening, since the unconventional catoptric light develops to a large extent on the image area by the grainy form. On the other hand, the conventional catoptric light is sensed more under no dampening, since the conventional catoptric light develops much by the ink applying the grainy form.

Figure 13C:
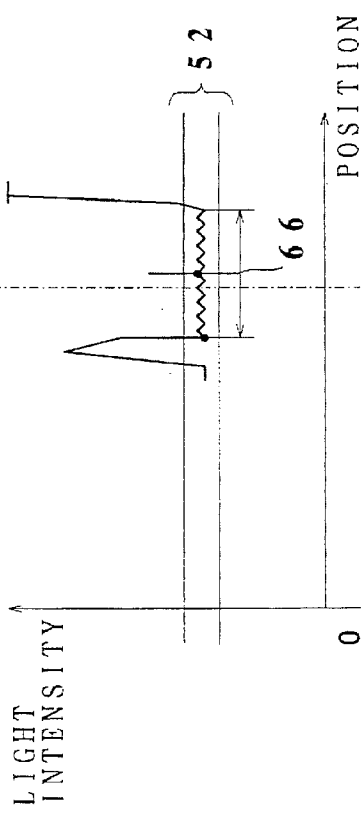

Next, a stabilized region is searched in a rotating direction. At step 206, controller 39 decides whether a region has a reference light intensity or not. The reference light intensity is defined by the light intensity sensed at a non-image area under no dampening. An example of such a light intensity is represented light intensity 52 shown in FIG. 13C. When the sensed light intensity is not the same as the reference light intensity, controller 39 repeats the execution of steps 202 through 206. On the other hand, when the sensed light intensity is the same as the reference light intensity, at step 208, controller 39 designates a region having the reference light intensity as the stabilized region. For example, in FIG. 13B a region corresponding to the range Q having light intensity 52 (see FIG. 13C) is the stabilized region on line 67. At step 210, controller 39 decides whether the range Q has a sufficient angle difference between the start angle and the stop angle of the non-image area. When the range Q has a sufficient angle difference, plate cylinder 5 rotates to a position substantially in the center of the width of the range Q, for example, position 65.

Figure 15:
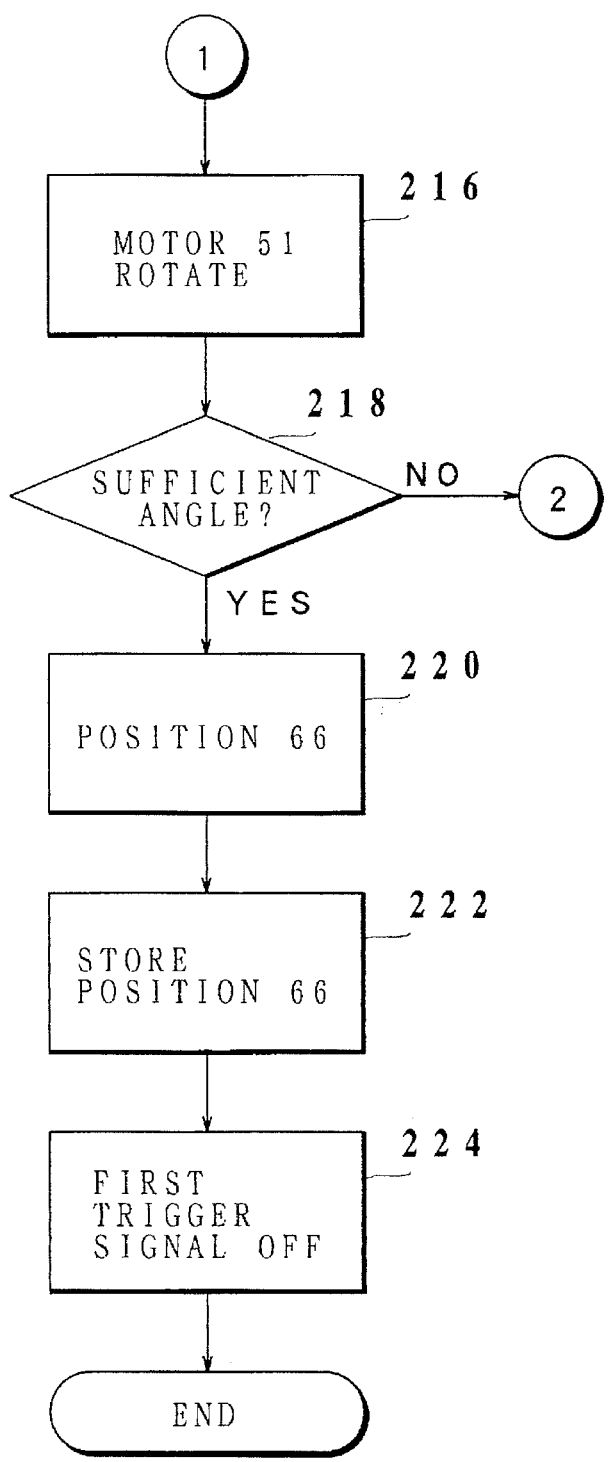
FIG. 15 is a flow chart of automatic mode for the dampening sensing apparatus of FIG. 11.

Second, a position of rotating direction is decided and will now be discussed with reference to FIG. 15. Supported rod 11a rotates when motor 51 is rotated upon receiving a driving signal from controller 39 (see FIGS. 11 and 12). At step 206, dampening volume sensing device 20 moves in parallel with an axis of plate cylinder 5 by traveling along slider 24. This is relationship between supported rod 11a and slider 24 is a screw pair which is defined by a two machine element relationship which accommodates rotating movement with linear movement. Dampening volume sensing device 20 senses light intensity upon receiving the radiation start signal from controller 39. At step 218, controller 39 determines the stabilized region and searches a width of the stabilized region on the line 69 (see FIG. 13A) in a similar fashion as mentioned above. In particular, at step 225, when the range in axis direction has a sufficient angle difference, slider 24 moves to a position substantially in the center of the width of the range, for example, position 66 (see FIG. 13C). At step 222, angle data representing the position 66 is stored in angle setting device 35 as setting angle data.

Dampening volume is sensed in the position 66. At step 224, controller 39 stops to issue the trigger signal when slider 24 moves to position 66. Dampening volume sensing device 20 then searches dampening volume upon receiving the trigger signal, as similarly described with respect to the manual setting mode. The automatic setting mode, however, releases the operator from searching the proposed area.

Referring back to FIG. 14, when the stabilized region is not searched, at step 212 controller 39 searches the stabilized region by rotating plate cylinder 5 when the range has a sufficient angle difference between the start angle and the stop angle at step 208. The execution of step 212 is repeated until plate cylinder 5 rotates on the rap when the stabilized region is not searched. At step 214, controller 39 issues a driving signal to motor 51 when the stabilized region is not searched even when plate cylinder 5 rotates on the rap, since the stabilized region is not on line 67. The sensed line is changed to another adjacent line by moving dampening volume sensing device 20 at step 210. The execution of steps 202 to 204 is repeated on the adjacent line. Also the execution of steps 202 to 216 is repeated when the stabilized region is not searched in the axis direction in step 210.

It is to be understood by one skilled in the art that order of the decision for determining the stabilized region is not critical. Although the embodiment shown decides whether the range in axis direction has a sufficient angle difference, after determining whether the range in rotating direction has a sufficient angle difference, another embodiment may determine whether the range in rotating direction has a sufficient angle difference, after determining whether the range in axis direction has a sufficient angle difference. Also another embodiment may determine whether the range in axis direction has a sufficient angle difference at the same time as determining whether the range in rotating direction has a sufficient angle difference.

As described above, dampening volume sensing apparatus 22 can search the proposed area easily because it automatically decides the area for sensing dampening volume.

Figure 16:
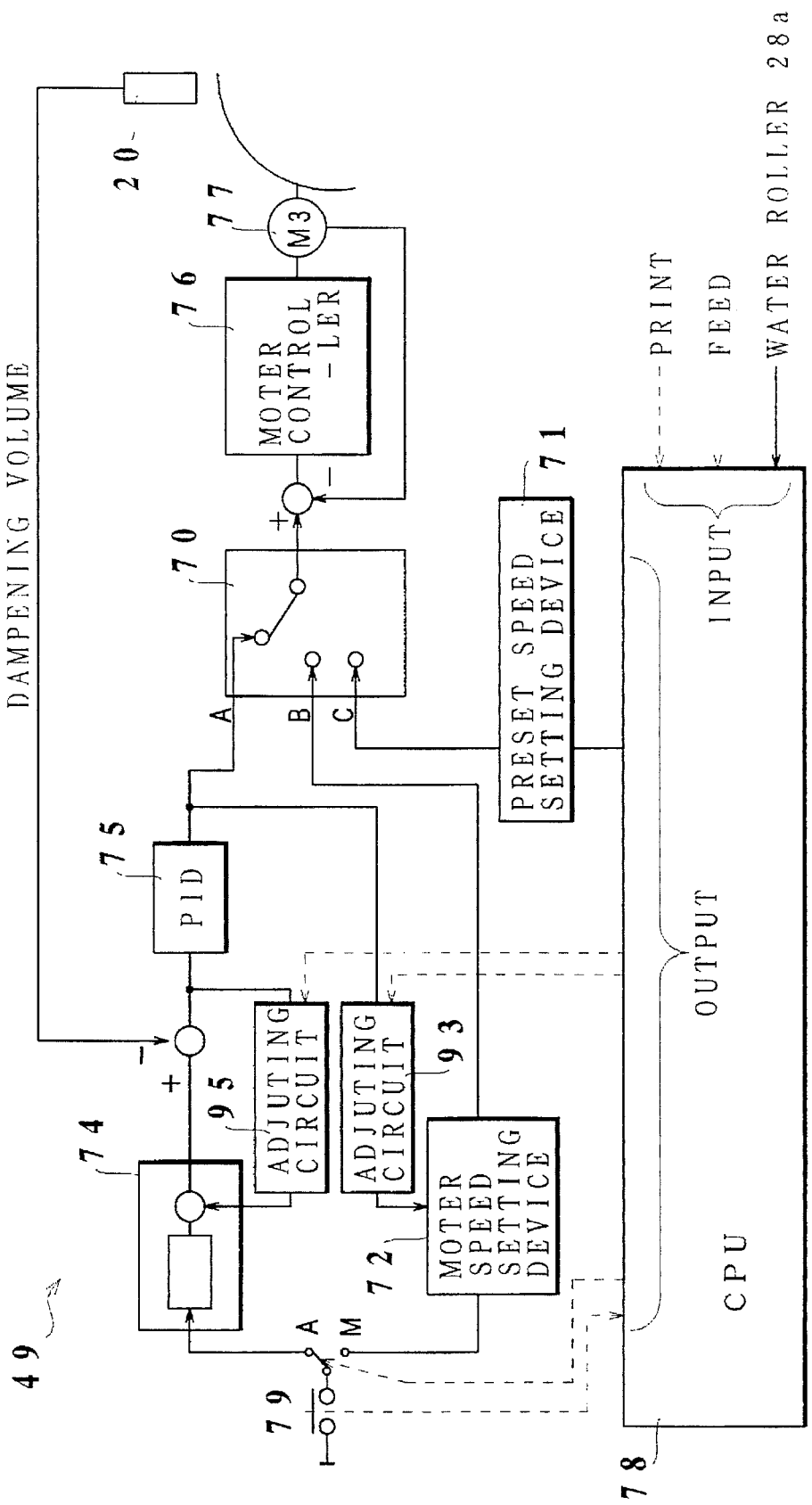
FIG. 16 is a block diagram of an embodiment of a dampening volume sensing apparatus in accordance with the present invention.

A dampening volume control apparatus 49 using dampening volume sensing device 20 will now be described. FIG. 16 shows a block diagram of dampening volume control apparatus 49. Dampening volume control apparatus 49 comprises a motor speed setting device 72 for setting the speed of motor 51 (see FIGS. 11 and 12) so that desired preparation dampening volume may be generated on printing preparation. It also comprises a dampening volume setting device 74, which acts as a storage mechanism for storing a desired dampening volume on printing, a PID 75 which acts as a means for generating an operation signal, a switching device 70, a motor controller 76 and a motor 77. In this embodiment, switching device 70 and a CPU 78 correspond to a switching mechanism. Also, motor controller 76 and motor 77 correspond to a means for controlling the supply of dampening volume. Referring back to FIG. 10, dampening volume is supplied to plate 13 through a roller 28d, a roller 28c, a roller 28b and a water roller 28a.

Dampening volume control of dampening volume control apparatus 49 will now be described. Dampening volume control apparatus 49 has three control modes, namely low speed mode, temporary much supply mode, and dampening volume holding mode.

The low speed mode is used for printing a preparation statement. FIGS. 17A and 17B show the relationship between the rotating speed of motor and dampening volume which is controlled by the control apparatus 49. Switching device 70 holds the statement of selecting point B by switching signal from CPU 78 in printing preparation, for example, until motor 77 starts rotating or water roller 28a (see FIG. 10) is on the plate. Dampening volume is controlled at the low speed mode as shown by range a in FIG. 17B since motor 77 is rotating at a predetermined speed stored in motor speed setting device 72. Dampening volume in plate 13 does not become saturated in printing preparation since the predetermined speed is sufficiently low.

The temporary much supply mode is used just before the printing statement. Switching device 70 changes the statement of selecting point C by the switching signal from CPU 78 as soon as water roller 28a is on. The volume of the preset speed setting device 71 is predetermined so as to supply a large dampening volume in a short time, so that the statement change is smooth from the printing preparation statement to the printing statement. Motor 77 is controlled by the temporary much supply mode (see range b in FIG. 17B). Motor 77 is rotated at a predetermined speed stored in motor speed setting device 72 after a predetermined short time upon receiving the signal for changing statement of selecting point C to statement of selecting point B from CPU 78.

The dampening volume holding mode is used for the printing statement. Printing is started as soon as water roller 28a rotates at the predetermined speed stored in motor speed setting device 72. Dampening volume is stabilized by balancing the supply dampening volume with dampening taken away from the plate when printing is started. CPU 78 issues a switching signal so that switching device 70 changes statement of selecting point B to statement of selecting point A. Therefore, dampening volume control apparatus 49 switches to the dampening volume holding mode. Motor 77 is controlled through motor controller 76 in the dampening volume holding mode (see range d in FIG. 17). PID 75 issues an operation signal representing an operation value calculated on the basis of the sensed dampening volume and the desired dampening volume (target volume). Motor 77 is controlled in accordance with the operation signal.

Dampening volume is adjusted in accordance with an order from the operator. The operator increases or decreases volume stored in dampening volume setting device 74 with a switch 79 after starting of the dampening volume holding mode so that dampening volume in the plate is suitable for printing. PID 75 controls motor 77 through motor controller 76 so that the adjusted dampening volume corresponds to the sensed dampening volume.

As described above, dampening volume control apparatus 49 can supply suitable dampening volume for printing without saturating dampening volume in printing preparation by switching between a low speed mode and a dampening volume holding mode. Moreover, statement change is smooth from the printing preparation statement to the printing statement because of the supply of a large dampening volume in a short time just before printing. Further, it is able to supply dampening volume as desired by an operator since the supplied dampening volume is accurately sensed by dampening volume sensing device 20 and is controlled with feedback control.

An adjusting circuit 93 (see FIG. 16) changes the desired preparation dampening volume generated by motor speed setting device 72 in preparation to discontinue printing for a period of time referred to as discontinuance time. The operation signal generated by PID 75 is transmitted to motor controller 76 through switching device 70 and to adjusting circuit 93. Adjusting circuit 93 generates an adjustment value on the basis of the operation signal generated by PID 75. Motor speed setting device 72 generates the preparation desired dampening volume changed by the adjustment value. In other words, adjusting circuit 93 changes the preparation desired dampening volume on the basis of the sensed dampening volume and the original dampening volume stored in adjusting circuit 93. The sensed dampening volume decreases since the water roller is off as a result of changing from the printing statement to the unprinting statement. The sensed dampening volume decreases inversely with an increase of the discontinuance time. Therefore, the error signal transmitted to PID 75 increases in proportion to the discontinuance time. The operation signal is generated and transmitted to adjusting circuit 93 based on the error signal. Dampening volume is supplied suitably in accordance with the discontinuance time (see range e in FIG. 17) since the error signal changes in accordance with the discontinuance time. Therefore, dampening volume control apparatus 49 provides control so as to quickly stabilize without regard to the discontinuance time.

As shown in FIG. 16, an adjusting circuit 95 can control with high following. The error signal is also transmitted to adjusting circuit 95. Adjusting circuit 95 generates an adjusting value based on the error signal quickly upon receiving an order from CPU 78. Dampening volume setting device 74 generates a value calculated by using the adjusting value and the original value. Adjusting circuit 95 particularly can control with high following when the error signal is large, for example, in printing start.

Dampening volume control apparatus 49 provides control so as to quickly stabilize without regard to the discontinuance time since dampening volume setting device 74 stores an optimum dampening volume.

Figure 18:
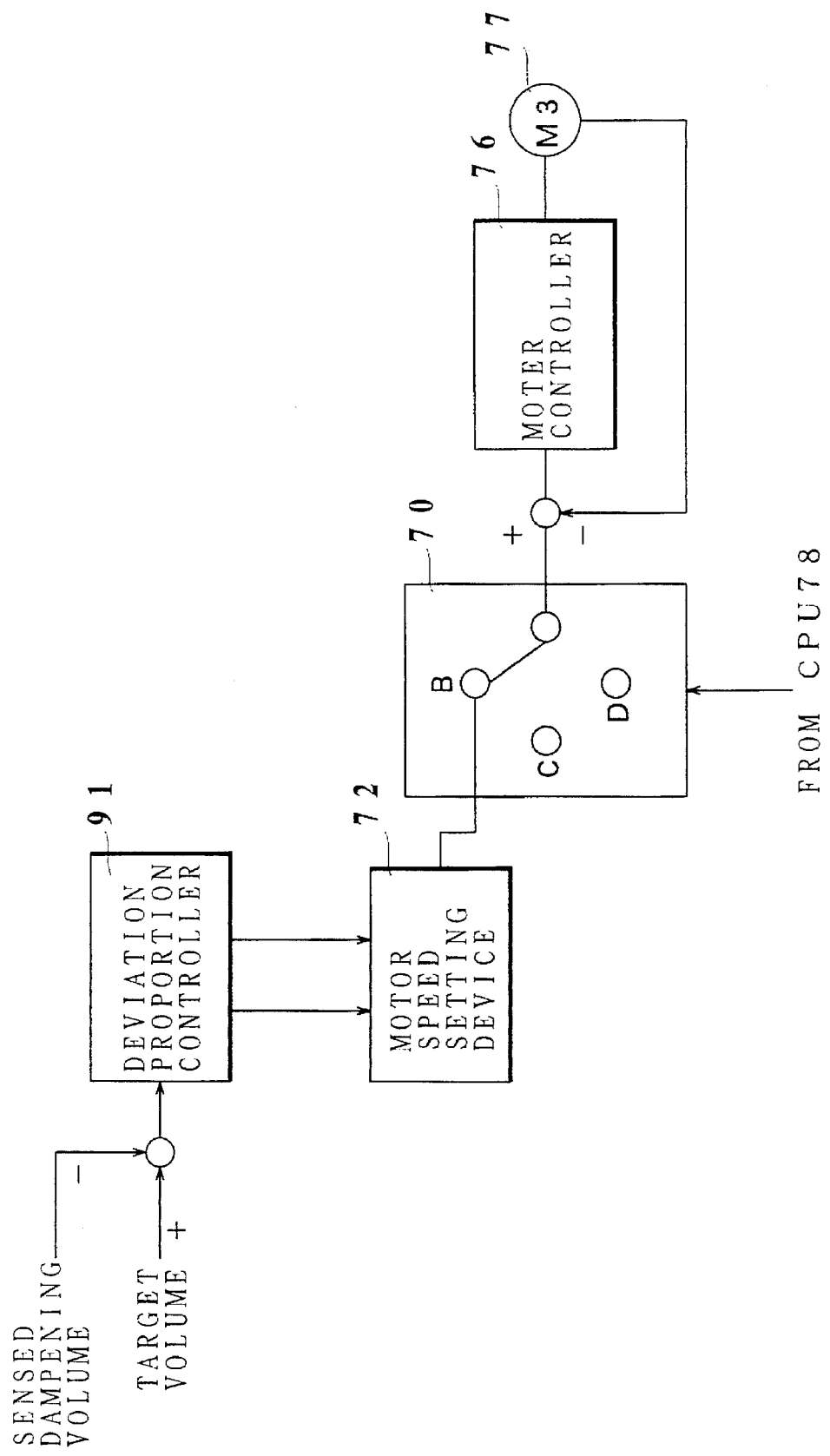
FIG. 18 is a block diagram of another embodiment of a dampening volume sensing apparatus in accordance with the present invention.

It is understood by those skilled in the art that the method of controlling the dampening volume is not limited to the embodiment above mentioned. Although in this embodiment PID 75 controls motor 77 at dampening volume holding mode, motor 77 may be controlled with digital control by CPU 78 or with deviation proportion control as shown in FIG. 18.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A dampening volume sensing device for an offset press comprising:

means for radiating light on a plate held on a plate cylinder upon receiving a radiation start signal, so as to form an irradiated area on said plate;

means for sensing substantially only conventional catoptric light reflected from said irradiated area and for generating a sensed signal representing a conventional catoptric light intensity; and calculating means for computing a dampening volume based on said sensed signal from said sensing means and for generating a dampening volume signal, not based on unconventional catoptric light, said radiating means being positioned with the device so that an incident angle of said radiating light respect to a surface of said irradiated area is made predetermined angle sufficient for changing said conventional catoptric light intensity sensed by said sensing means in accordance with said dampening volume signal, the irradiated area having a size from 10 mm$^2$ to 90 mm$^2$ that is selected so that the conventional catoptric light can be sensed by the means for sensing irrespective of a grainy form of the plate.

2. A dampening volume sensing device according to claim 1, wherein said incident angle ranges from 65° to 85°.

3. A dampening volume sensing device according to claim 1, wherein said incident angle ranges from 70° to 80°.

4. A dampening volume sensing device according to claim 1, wherein said incident angle is about 75°.

5. A dampening volume sensing device according to claim 1, wherein said size of said irradiated area ranges from an area between 30 mm$^2$ to 70 mm$^2$.

6. A dampening volume sensing device according to claim 1, wherein said size of said irradiated area is an area of about 50 mm$^2$.

7. A dampening volume sensing method for an offset press comprising the steps of:

radiating light on a plate held on a plate cylinder upon receiving a radiation start signal so as to form an irradiated area on said plate;

sensing substantially only conventional catoptric light reflected from said irradiated areas and generating a sensed signal representing a conventional catoptric light intensity;

computing a dampening volume based on said sensed signal; and generating a dampening volume signal; said radiating step being radiated so that an incident angle of said radiating light with respect to a surface of said irradiated area is made at a predetermined angle sufficient for changing said conventional catoptric light intensity in accordance with said dampening volume signal, the irradiated area having a size from 10 mm$^2$ to 90 mm$^2$ that is selected so that the conventional catoptric light can be sensed irrespective of a grainy form of the plate.

8. A dampening volume sensing apparatus comprising:

a dampening volume sensing device, said dampening volume sensing device comprising:

means for radiating light on a plate held on a plate cylinder upon receiving a radiation start signal, so as to form an irradiated area on said plate;

means for sensing substantially only conventional catoptric light reflected from said irradiated area and for generating a sensed signal representing a conventional catoptric light intensity;

calculating means for computing a dampening volume based on said sensed signal from said sensing means and for generating a dampening volume signal, wherein said radiating means positioned with the device so that an incident angle of said radiating light with respect to a surface of said irradiated area is made at a predetermined angle sufficient for changing said conventional catoptric light intensity sensed by said sensing means in accordance with said dampening volume signal, and wherein said irradiated area has a size from 10 mm$^2$ to 90 mm$^2$ such that conventional catoptric light can be sensed by said sensing means irrespective of a grainy form of said plate;

means for driving said plate cylinder, said dampening volume sensing device being supported so as to be able to move in parallel with an axis of said plate cylinder;

aiming means for searching for a proposed area for irradiating with said radiating means, means for sorting a positional phase defined between said proposed area and an area radiated by said dampening volume sensing device;

means for detecting a rotating phase of said plate cylinder; and means for transmitting said radiation start signal to said dampening volume sensing device based on said detected rotating phase of said plate cylinder and said positional phase so as to radiate light on said proposed area in synchronization with the rotation of said plate cylinder.

9. A dampening volume sensing apparatus for an offset press comprising:

a dampening volume sensing device, said dampening volume sensing device comprising:

means for radiating light on a plate held on a plate cylinder upon receiving a radiation start signal, so as to form an irradiated area on said plate;

means for sensing substantially only conventional catoptric light reflected from said irradiated area and for generating a sensed signal representing a conventional catoptric light intensity;

calculating means for computing a dampening volume based on said sensed signal from said sensing means and for generating a dampening volume signal, wherein said radiating means positioned with the device so that an incident angle of said radiating light with respect to a surface of said irradiated area is made at a predetermined angle sufficient for changing said conventional catoptric light intensity sensed by said sensing means in accordance with said dampening volume signal, and wherein said irradiated area has a size from 10 mm$^2$ to 90 mm$^2$ such that conventional catoptric light can be sensed by said sensing means irrespective of a grainy form of said plate;

means for driving said plate cylinder;

means for moving said dampening volume sensing device in parallel with an axis of said plate cylinder;

means for storing a reference light intensity which is detected in a non-image area under a no dampening condition on said plate;

searching means for transmitting the radiation start signal to said dampening volume sensing device and for search for a proposed area of said plate which has a light intensity substantially the same as said reference light intensity and which is wider than said irradiated area, by comparing said reference light intensity with a light intensity detected by said dampening volume sensing device; and means for generating said radiation start signal to said radiating means of said dampening volume sensing device so as to radiate said radiating area in synchronization with the rotation of said plate cylinder.

10. A dampening volume sensing apparatus according to claim 9, wherein said searching means searches said proposed area by searching an axis direction position behind a rotate direction position, said rotate direction position being determined at substantially the center of a width of said non-image area when said width of said non-image area is wider than that of said irradiated area, said axis direction position being determined at substantially the center of a width of said non-image area when said width of said non-image area is wider than that of said irradiated area.

11. A dampening volume controlling apparatus for an offset press comprising:

a dampening volume sensing device, said dampening volume sensing device comprising:

means for radiating light on a plate held on a plate cylinder upon receiving a radiation start signal, so as to form an irradiated area on said plate;

means for sensing substantially only conventional catoptric light reflected from said irradiated area and for generating a sensed signal representing a conventional catoptric light intensity;

calculating means for computing a dampening volume based on said sensed signal from said sensing means and for generating a dampening volume signal, wherein said radiating means positioned with the device so that an incident angle of said radiating light with respect to a surface of said irradiated area is made at a predetermined angle sufficient for changing said conventional catoptric light intensity sensed by said sensing means in accordance with said dampening volume signal, and wherein said irradiated area has a size from 10 mm$^2$ to 90 mm$^2$ such that conventional catoptric light can be sensed by said sensing means irrespective of a grainy form of said plate;

means for inputting a desired dampening volume for printing;

means for generating an operation signal based on said dampening volume sensed by said dampening volume sensing device and said desired dampening volume; and means for controlling a supply dampening volume to said plate in accordance with said operation signal, so that said sensed dampening volume is approximately the same as said desired dampening volume on printing.

12. A dampening volume control apparatus according to claim 11, further comprising:

means for generating a desired preparation dampening volume for printing preparation; and means for switching alternatively between said desired preparation dampening volume and said desired dampening volume and for applying to said controlling means said switching means being provided between said operation signal generating means and said controlling means.

13. A dampening volume control apparatus according to claim 12, further comprising:

means for changing said desired preparation dampening volume in accordance with said sensed dampening volume and said desired dampening volume on printing.

14. A dampening volume sensing device for an offset press comprising:

means for radiating light on a plate held on a plate cylinder upon receiving a radiation start signal, so as to form an irradiated area on said plate;

means for sensing substantially only conventional catoptric light reflected from said irradiated area and for generating a sensed signal representing a conventional catoptric light intensity, said sensing means comprising only a single sensor for receiving light from the means for radiating light; and calculating means for computing a dampening volume based on said sensed signal from said sensing means and for generating a dampening volume signal, said radiating means being positioned with the device so that an incident angle of said radiating light with respect to a surface of said irradiated areas is made at a predetermined angle sufficient for changing said conventional catoptric light intensity sensed by said sensing means in accordance with said dampening volume signal, the irradiated area having a size from 10 mm$^2$ to 90 mm$^2$ that is selected so that the conventional catoptric light can be sensed by the means for sensing irrespective of a grainy form of the plate.

15. A dampening volume sensing device for an offset press comprising:

a light source for radiating light on a plate held on a plate cylinder upon receiving a radiation start signal, so as to form an irradiated area on said plate;

a sensor for sensing substantially only conventional catoptric light reflected from said irradiated area and for generating a sensed signal representing a conventional catoptric light intensity; and a calculator for computing a dampening volume based on said sensed signal from said sensor and for generating a dampening volume signal, not based on unconventional catoptric light, said light source being positioned with the device so that an incident angle of said radiating light respect to a surface of said irradiated area is made a predetermined angle sufficient for changing said conventional catoptric light intensity sensed by said sensor in accordance with said dampening volume signal, the irradiated area having a size from 10 mm$^2$ to 90 mm$^2$.

* * * * *